(12) United States Patent
Kerr (10) Patent No.: US 7,502,639 B2
(45) Date of Patent: Mar. 10, 2009

(54) ANALYSIS OF RETINAL METABOLISM OVER AT LEAST A PORTION OF A CARDIAC CYCLE

(76) Inventor: Patrick Kerr, 9 The Chase, Reigate, Surrey (GB) RH2 7DJ ( * ) Notice: Subject to any disclaimer, the term of this patent is extended or adjusted under 35 U.S.C. 154(b) by 668 days.

(21) Appl. No.: 11/150,950

(22) Filed: Jun. 13, 2005

(65) Prior Publication Data

US 2005/0288565 A1   Dec. 29, 2005

(30) Foreign Application Priority Data

Jun. 29, 2004   (GB)   ................................. 0414570.2

(51) Int. Cl.
*A61B 5/1455*   (2006.01)
(52) U.S. Cl. ................... 600/318; 600/320; 600/322
(58) Field of Classification Search ................. 600/318, 600/320, 322, 323, 340; 351/206
See application file for complete search history.

(56) References Cited

U.S. PATENT DOCUMENTS 6,244,712 B1 *  6/2001  Smith et al. ................. 351/221
2003/0088165 A1  5/2003  Smith et al.

FOREIGN PATENT DOCUMENTS

GB   2375679   11/2002

* cited by examiner

*Primary Examiner*—Eric F Winakur
*Assistant Examiner*—Etsub D Berhanu
(74) *Attorney, Agent, or Firm*—Seyfarth Shaw LLP (57) ABSTRACT

Retinal metabolism is analyzed with a retinal function camera over at least a portion of a cardiac cycle by first illuminating a portion of a retina of an eye 10 with light of a first wavelength and producing a first image. The portion of the retina is subsequently illuminated with light of a second wavelength, the first and second wavelengths being selected such that absorptivity of light of the first wavelength by oxygenated blood is greater than absorptivity of light of the second wavelength and the absorptivity of light of the first wavelength by deoxygenated blood is less than absorptivity of light of the second wavelength, to produce a second image. The first and second images are processed to map relative oxygenation of the portion of the retina as an indication of retinal metabolic function of the portion of the retina. The procedure is repeated over at least a portion of a cardiac cycle to analyze metabolic function changes of the portion of the retina within the at least a portion of a cardiac cycle. In some embodiments at least a portion of the retina is subjected to optical stimulation and effects of the optical stimulation on retinal metabolic function analyzed.

50 Claims, 1 Drawing Sheet

Figure 1

ANALYSIS OF RETINAL METABOLISM OVER AT LEAST A PORTION OF A CARDIAC CYCLE

FIELD OF THE INVENTION

This invention relates to analysis of retinal metabolism over at least a portion of a cardiac cycle to provide an objective assessment of retinal metabolism. In an embodiment of the invention retinal metabolic response to optical stimuli is determined.

BACKGROUND OF THE INVENTION

The retina is a complex structure that contains photoreceptor cells, a network of nerve cells, blood vessels and a metabolically active retinal pigment epithelium. Common retinal diseases that affect retinal metabolism include age-related macular degeneration, diabetic retinopathy and glaucoma, which may cause visual loss and blindness.

Known retinal imaging technology provides some structural and functional information about retinal function and hence retinal diseases.

Thus a scanning laser ophthalmoscope disclosed in R. H. Webb, G. W. Hughes, and O. Pomerantzeff, Flying spot TV ophthalmoscope, Applied Optics 19, 2991-2997, 1980, uses a laser scanning light source to image a retina, subsequently combined with a confocal optical filter to select some light reflected from the retina.

Scanning laser ophthalmoscope indirect mode imaging, for analysing indirectly-reflected light, which uses an annular aperture and stop to block on-axis reflections to form an image from laterally scattered light reflections, is disclosed in Ann E Elser, Stephen A. Burns, John J Weitter, Francois C Delori, Infrared imaging of sub-retinal structures in the human ocular fundus, Vision Res. Vol. 36, No 1, pp. 191-205, 1996.

Retinal oximetry produces a numerical value measurement of the percentage oxygen saturation of blood in retinal arteries and veins. A small region of multi-spectral retinal images of a retinal blood vessel and small adjacent region of the retina is selected for analysis and a numerical percentage oxygen saturation of blood in the blood vessel calculated.

The retinal metabolic image changes over the duration of a heartbeat. With the arrival of a retinal arterial pulse there is an increase of retinal haemoglobin oxygenation. This is followed by a fall in retinal haemoglobin oxygenation, due to oxygen consumption within the metabolically active retinal tissue, before the next retinal arterial pulse.

U.S. Pat. No. 6,244,712 discloses optical scanning spectroscopic retinal blood vessel oximetry using a plurality of wavelengths to illuminate successive portions of the retina and form an interlaced retinal data frame, to avoid over-illuminating an eye by scanning with the plurality of wavelengths simultaneously. The interlaced retinal data frame may be de-interlaced to form plural monochromatic retinal images corresponding to the respective wavelengths. Signals from the eye may be filtered or selected with confocal or anti-confocal filters before being delivered to a detector. The laser scans may be triggered, for example in response to an r-wave of an electrocardiogram, at a predetermined point in a cardiac cycle thereby permitting a detailed analysis of one or more phases of the cardiac cycle.

US 2002/0188203 discloses measurement of blood oxygen saturation in a retinal blood vessel by detecting light that has made a single pass through the retinal blood vessel, i.e. retinal vein or artery, and then been diffused laterally through retinal and/or choroidal layers and left the eye without again passing through the retinal blood vessel. An anti-confocal optical filter, with an aperture and central stop, is used to isolate such single-pass optical signals and thereby simplify calculation of retinal blood oxygen saturation, resulting in increased accuracy of measurement of oxygen saturation. This provides an objective assessment of retinal haemoglobin oxygenation within a small portion of the retinal blood vessel. It is suggested that such measurements can be used to monitor cardiac output of a subject or detect and determine a rate of blood loss.

A retinal metabolic image changes in response to a light stimulus of the retina caused by an increase in retinal neuronal metabolic activity and therefore of oxygen consumption.

US 2004/0075812 discloses detection of changes in reflectance of near-infrared light from the retina of human subjects, caused by changes in oxygen saturation in response to visual activation of the retina by a light pattern or other light stimulus. This provides an objective assessment of inner retinal function, allowing detection, at an early stage, of a regional defect caused by glaucoma.

Haemoglobin oxygenation saturation light absorption is disclosed by, Van Assendelft OW. Spectrophotometry of haemoglobin derivatives. Royal Vangorcum, Assen, The Netherlands: Thomas, 1970.

WO 02/080759 discloses a retinal function camera in which use of isoreflective points enables isolation of retinal haemoglobin oxygenation image data from multi-spectral retinal images, and formation of a retinal metabolic image based on haemoglobin oxygenation. The retinal metabolic image provides a subjective assessment of retinal haemoglobin oxygenation image data captured within the imaging time period. The retinal function image may be synchronised with an R wave of a subject's electrocardiogram, to study retinal metabolism at a predetermined time in a cardiac cycle of the subject. That is, a predetermined time delay may be allowed between detection of the R wave and formation of a scanned image.

The prior art, therefore, provides: oximetry, an objective assessment of retinal haemoglobin oxygenation within a small portion of a retinal blood vessel; an objective assessment of infrared light reflectance change of the retina to light stimulus; and a subjective assessment of retinal haemoglobin oxygenation image data. The prior art does not provide an objective assessment of retinal metabolism based on haemoglobin oxygenation.

SUMMARY OF THE INVENTION

According to a first aspect of the present invention, there is provided a method of analysing retinal metabolism over at least a portion of a cardiac cycle, the method comprising the steps of: a) illuminating a portion of a retina of an eye with light of a first wavelength; b) producing a first image of the portion of the retina illuminated with the light of the first wavelength; c) illuminating the portion of the retina with light of a second wavelength, the first and second wavelengths being selected such that absorptivity of light of the first wavelength by oxygenated blood is greater than absorptivity of light of the second wavelength and the absorptivity of light of the first wavelength by deoxygenated blood is less than absorptivity of light of the second wavelength; d) producing a second image of the portion of the retina illuminated with the light of the second wavelength; e) processing the first and second images with image processing means to map relative oxygenation of the portion of the retina as an indication of retinal metabolic function of the portion of the retina; and f) repeating steps a) to e) within the at least a portion of a cardiac cycle to analyse metabolic function changes of the portion of the retina to detect a haemoglobin oxygenation image data retinal arterial waveform within the at least a portion of a cardiac cycle to provide synchronisation with a cardiac cycle of a subject for analysing retinal metabolic image data over the at least a portion of the cardiac cycle.

Conveniently, the step of illuminating the portion of the retina with light of a first wavelength comprises providing a first light source and emitting light of the first wavelength and providing scanning means to produce a scanning beam and scanning the portion of the retina with light from the first light source.

Advantageously, the step of illuminating the portion of the retina with light of a second wavelength comprises providing: a second light source and emitting light of the second wavelength and first optical beam combiner means and selectively directing light from the first light source and from the second light source to the scanning means to produce a scanning beam and scanning the portion of the retina with light from the second light source subsequently to scanning the portion of the retina with light from the first light source.

Conveniently, at least one of the first light source and the second light source is synchronised with the scanning means.

Conveniently, the method includes a further step of providing first focusing means and focusing the scanning beam from the scanning means onto the at least a portion of the retina with the first focusing means.

Advantageously, the method includes a step of providing refractive error correcting means and correcting for refractive errors of the eye with the refractive error correcting means, to permit focusing of the scanning beam on the at least a portion of the retina.

Conveniently, the step of providing refractive error correcting means comprises providing adaptive optics and correcting for optical aberrations of the eye.

Advantageously, the step of providing refractive error correcting means comprises providing wave-front sensor means and wave-front compensation means.

Conveniently, the step of providing wave-front compensation means comprises providing deformable mirror means.

Conveniently, the step of producing first and second images includes providing beam splitter means for splitting a beam reflected from the at least a portion of the retina when illuminated by light of the first wavelength and light of the second wavelength to form a split beam; image sensor means and second focusing means and focusing the split beam on the image sensor means for sensing an image of the at least a portion of the retina and image capture means for capturing the sensed image.

Advantageously, the step of providing image capture means comprises providing frame grabber means.

Advantageously, the scanning means is synchronised with at least one of the image sensor means, the image capture means and the image processing means.

Conveniently, the step of illuminating the portion of the retina with light of the first wavelength comprises illuminating the portion of the retina with light of wavelengths centred on one of 830 nm, 850 nm and 910 nm.

Conveniently, the step of illuminating the portion of the retina with light of the second wavelength comprises illuminating the portion of the retina with light of wavelengths centred on one of 635 nm, 670 nm and 760 nm.

Conveniently, the step of processing the first and second images comprises determining isoreflective points of the respective images at which absorption of light of the first wavelength is substantially equal to absorption of light of the second wavelength and determining areas of the respective images having differential absorptivity for the first and second wavelengths; isolating haemoglobin oxygenation image data from the first and second wavelength images by subtracting the isoreflective point from respective first and second wavelength images, the contrast of each portion of the processed images thereby being proportional to a difference in oxygenation of that portion of the processed images from the oxygenation of the isoreflective point, to obtain retinal metabolic image data based on haemoglobin oxygenation.

Advantageously, step f) further comprises determining from the metabolic function changes a waveform reference point in a haemoglobin oxygenation image data waveform corresponding to a cardiac cycle.

Conveniently, the step of determining a waveform reference point comprises determining an amplitude trough between a trailing edge and a leading edge of an arterial pulse of the haemoglobin oxygenation image data waveform.

Optionally, the step of determining a waveform reference point comprises determining an amplitude peak of an arterial pulse of the haemoglobin oxygenation image data waveform.

Optionally, the step of determining a waveform reference point comprises determining an inflection point between an amplitude trough and an amplitude peak of an arterial pulse of the haemoglobin oxygenation image data waveform.

Conveniently, the method is adapted for determining oxygenation changes associated with the cardiac cycle.

Conveniently, the method is adapted for determining characteristics of at least one of amplitude, pattern, shape and duration of the cardiac cycle.

Advantageously, the step of determining oxygenic changes comprises using Fourier analysis for determining a cardiac cycle waveform.

Advantageously, step f) further comprises subtracting effects of changes in oxygenation caused by the cardiac cycle to determine metabolic function of the at least a portion of the retina independently of oxygenation changes caused by the cardiac cycle.

Advantageously, the method includes a further step of subjecting the at least a portion of the retina to optical stimulation and analysing effects of the optical stimulation on retinal metabolic function.

Conveniently, the optical stimulation of the at least a portion of the retina is synchronised with reference to the waveform reference point.

Advantageously, step f) further comprises subtracting effects of changes in oxygenation caused by the cardiac cycle from the effects of changes in oxygenation caused by the optical stimulation to isolate changes in retinal metabolism caused by the optical stimulation.

Advantageously, the method further comprises analysing isolated responses of retinal metabolism caused by the optical stimulation to determine waveform characteristics of at least one of latency between the optical stimulation and the retinal metabolism response, amplitude, pattern, shape and duration of the response.

Conveniently, the step of subjecting the at least a portion of the retina to optical stimulation comprises providing an optical signal stimulus light source; and second beam combining means and combining a light beam from the optical signal stimulus light source selectively with one of light of the first wavelength and light of the second wavelength.

Advantageously, the step of providing an optical signal stimulus light source comprises providing an array of light-emitting diodes and one of simultaneously or sequentially stimulating a plurality of points on the at least a portion of the retina.

Conveniently, the optical signal stimulus light source is modulated to generate an optical signal stimulus pattern on the at least a portion of a retina.

Conveniently, the optical signal stimulus light source comprises an optical signal stimulus laser.

Advantageously, the method is adapted for determining cardiac function.

Advantageously, the method is adapted for determining cerebral arterial circulatory function.

Conveniently the method is adapted for evaluating effects of therapeutic agents on retinal metabolism.

Conveniently the method is adapted for evaluating effects of therapeutic agents on retinal metabolic response to optical stimulation.

According to a second aspect of the invention, there is provided a retinal function camera comprising: a first source of light of a first wavelength band; a second source of light of a second wavelength band, the absorptivity of light of the first wavelength band by oxygenated blood being greater than the absorptivity of light of the second wavelength band and the absorptivity of light of the first wavelength band by deoxygenated blood being less than the absorptivity of light of the second wavelength band; an optical signal stimulus light source; means for focusing light from the optical signal stimulus light source and selectively from the first and second sources onto a portion of a retina of an eye; imaging means for producing respective images of the portion of the retina illuminated with the respective wavelength bands and stimulated by the optical signal stimulus light source; and image processing means adapted to process the respective images obtained by the imaging means to determine isoreflective points of the respective images at which absorption of light of the first wavelength is substantially equal to absorption of light of the second wavelength and areas of the respective images having differential absorptivity for the first and second wavelengths, repeatedly to obtain a retinal function image based on haemoglobin oxygenation within at least a portion of a cardiac cycle to analyse metabolic functional changes of the portion of the retina to detect a haemoglobin oxygenation image data retinal arterial waveform within the at least a portion of a cardiac cycle to provide synchronisation with a cardiac cycle of a subject for analysing retinal metabolic image data over the at least a portion of the cardiac cycle when the retina is subjected to optical stimulation.

Conveniently, the optical signal stimulus light source comprises an optical signal stimulus laser.

Conveniently, the retinal function camera further comprises scanning means arranged for producing a scanning beam for scanning the portion of the retina with light from the optical signal stimulus light source and selectively from the first and second sources.

Advantageously, the retinal function camera further comprises first optical beam combiner means arranged for selectively directing light from the first light source and from the second light source to the scanning means.

Advantageously, the retinal function camera further comprises first synchronisation means arranged for synchronising at least one of the first light source and the second light source with the scanning means.

Advantageously, the retinal function camera further comprises refractive error correcting means arranged for correcting for refractive errors of the eye to permit focusing of the scanning beam on the at least a portion of the retina.

Conveniently, the refractive error correcting means comprises adaptive optics arranged for correcting for optical aberrations of the eye.

Conveniently, the refractive error correcting means comprises wave-front sensor means and wave-front compensation means.

Advantageously, the wave-front compensation means comprises deformable mirror means.

Conveniently, the retinal function camera further comprises beam splitter means arranged for splitting a beam reflected from the at least a portion of the retina when illuminated by light of the first wavelength band and light of the second wavelength band to form a split beam; image sensor means and second focusing means arranged for focusing the split beam on the image sensor means for sensing an image of the at least a portion of the retina and image capture means for capturing the sensed image.

Conveniently, the image capture means comprises frame grabber means.

Advantageously, the retinal function camera further comprises second synchronisation means arranged for synchronising at least one of the image sensor means, the image capture means and the image processing means with the scanning means.

Conveniently, the first wavelength band comprises wavelengths centred on one of 830 nm, 850 nm and 910 nm.

Conveniently, the second wavelength band comprises wavelengths centred on one of 635 nm, 670 nm and 760 nm.

According to a third aspect of the invention, there is provided computer executable software code stored on a computer readable medium, the code being for analysing retinal metabolism over at least a portion of a cardiac cycle, comprising the steps of: a) illuminating a portion of a retina of an eye with light of a first wavelength; b) producing a first image of the portion of the retina illuminated with the light of the first wavelength; c) illuminating the portion of the retina with light of a second wavelength, the first and second wavelengths being selected such that absorptivity of light of the first wavelength by oxygenated blood is greater than absorptivity of light of the second wavelength and the absorptivity of light of the first wavelength by deoxygenated blood is less than absorptivity of light of the second wavelength; d) producing a second image of the portion of the retina illuminated with the light of the second wavelength; e) processing the first and second images with image processing means to map relative oxygenation of the portion of the retina as an indication of retinal metabolic function of the portion of the retina; and f) repeating steps a) to e) within the at least a portion of a cardiac cycle to analyse metabolic function changes of the portion of the retina to detect a haemoglobin oxygenation image data retinal arterial waveform within the at least a portion of a cardiac cycle to provide synchronisation with a cardiac cycle of a subject for analysing retinal metabolic image data over the at least a portion of the cardiac cycle.

According to an fourth aspect of the invention, there is provided one or more programmed computers for analysing retinal metabolism over at least a portion of a cardiac cycle comprising the steps of: a) illuminating a portion of a retina of an eye with light of a first wavelength; b) producing a first image of the portion of the retina illuminated with the light of the first wavelength; c) illuminating the portion of the retina with light of a second wavelength, the first and second wavelengths being selected such that absorptivity of light of the first wavelength by oxygenated blood is greater than absorptivity of light of the second wavelength and the absorptivity of light of the first wavelength by deoxygenated blood is less than absorptivity of light of the second wavelength; d) producing a second image of the portion of the retina illuminated with the light of the second wavelength; e) processing the first and second images with image processing means to map relative oxygenation of the portion of the retina as an indication of retinal metabolic function of the portion of the retina; and f) repeating steps a) to e) within the at least a portion of a cardiac cycle to analyse metabolic function changes of the portion of the retina to detect a haemoglobin oxygenation image data retinal arterial waveform within the at least a portion of a cardiac cycle to provide synchronisation with a cardiac cycle of a subject for analysing retinal metabolic image data over the at least a portion of the cardiac cycle.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the accompanying drawing in which.

DETAILED DESCRIPTION OF EMBODIMENTS

Throughout the description, identical reference numerals are used to identify like parts.

Figure 1:
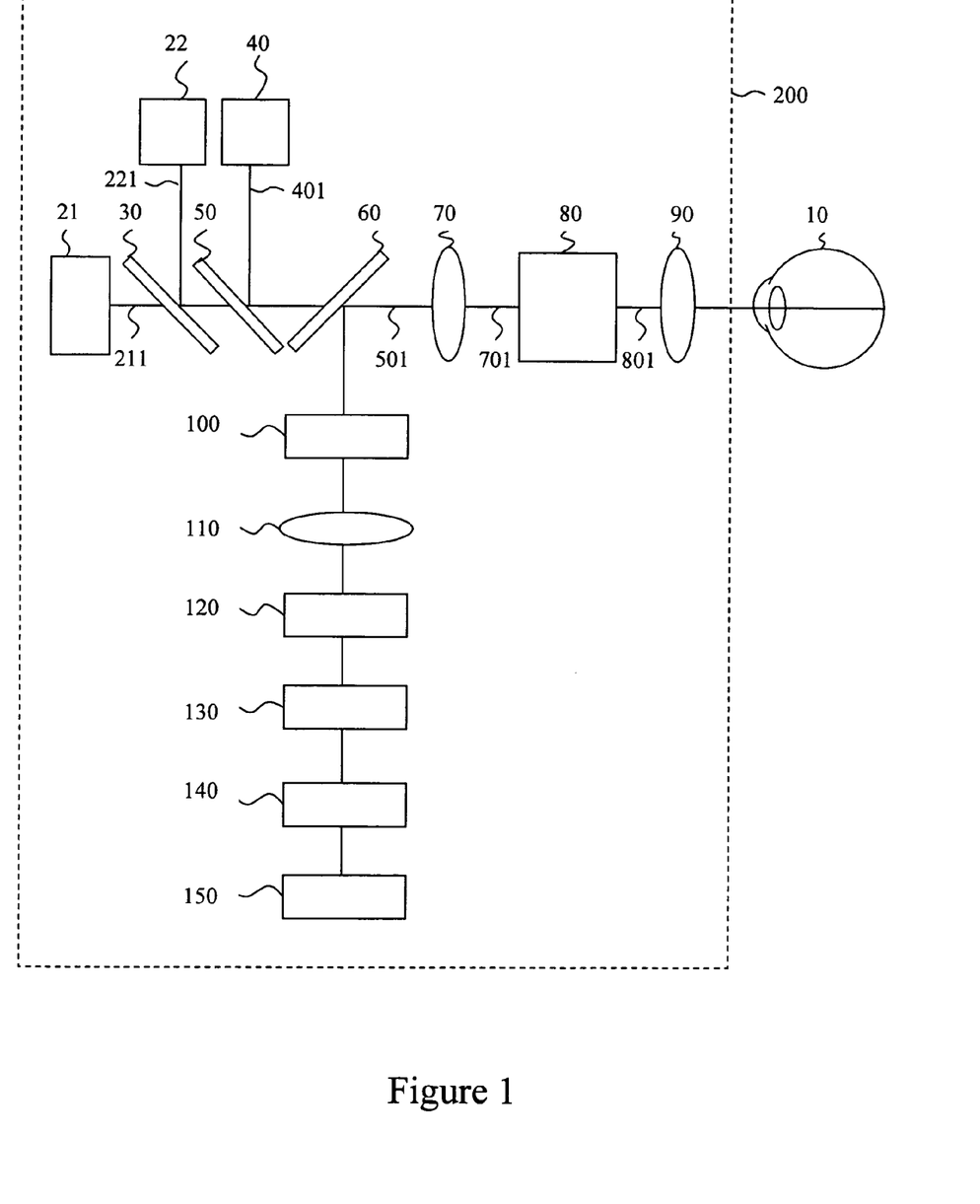
FIG. 1 is a schematic diagram of an apparatus according to the invention.

A retinal function camera 200 according to the invention, as shown in FIG. 1, has arranged sequentially on a first optical axis: a first light source 21 for emitting light of a first wavelength, a first optical beam combiner 30, a second optical beam combiner 50, an optical beam splitter 60, a first focusing lens 70, a vertical and horizontal optical beam scanner 80 and an imaging lens 90. A second light source 22, for alternatively emitting light of a second wavelength different from the first wavelength, is arranged so that light from the second light source incident on the first optical beam combiner 30 is alternatively transmittable along the first optical axis. An optical signal stimulus laser 40 is arranged so that light selectively emitted from the optical signal stimulus laser and incident on the second optical beam combiner 50 is transmittable along the first optical axis.

The optical beam splitter 60 is also located on a second optical axis, substantially perpendicular to the first optical axis. Sequentially arranged on the second optical axis, downstream from the optical beam splitter 60, are an orthogonal polarising filter 100, a second focusing lens 110, a confocal optical filter 120 and an image sensor 130. The imaging sensor may be a photomultiplier tube, an avalanche photodiode, a CCD imaging sensor or a CMOS imaging sensor. Operationally coupled to the image sensor is a frame grabber 140, and operationally coupled to the frame grabber 140 is an image processor 150. As an alternative to the frame grabber, any other known device for capturing the image may be provided.

One or more of the optical components may optionally be coupled by one or more optical fibres respectively (not shown) in either or both of illuminating and imaging paths, so that the coupled components are not necessarily physically aligned on one of the optical axes.

An endoscope arrangement may alternatively be used.

Moreover, although the first optical axis is shown schematically as substantially perpendicular to the second optical axis, it will be understood that other relative orientations of the axes may be employed.

The first and second light sources 21, 22 are provided such that absorptivity of light emitted by the first light source by oxygenated blood is greater than absorptivity of light emitted by the second light source and the absorptivity of light emitted by the first light source by deoxygenated blood is less than absorptivity of light emitted by the second light source. The first light source 21 and the second light source 22 emit light with respective wavelengths preferably in a range between 488 nm and 1000 nm. The first light source 21 emits wavelengths preferably centred substantially on one of 830 nm, 850 nm and 910 nm. The second light source 22 emits wavelengths preferably centred substantially on one of 635 nm, 670 nm and 760 nm. The first light source 21 is preferably a laser or a superluminescent diode and the second light source 22 is also preferably a laser or a superluminescent diode.

In use, light from the first light source 21 and the second light source 22 is sequentially scanned over a same portion of the retina of an eye 10 of a subject. The portion of the retina may be, for example, a pixel, a line scan or a complete image scan.

In detail, a first incident light beam 211 emitted by the first light source 21 is incident on a first face of the first optical beam combiner 30 at a first angle of incidence of substantially 45 degrees, such that the light beam is transmitted through the first optical beam combiner to be incident on, and pass through, the second optical beam combiner 50. The light beam then passes sequentially through the optical beam splitter 60 and a focus lens 70 for correcting for refractive errors of the eye 10, to permit eventual focusing of the light beam on a retina of the eye 10. The corrected light beam is incident on a vertical and horizontal scanner 80 and subsequently focused by the imaging lens 90 on the retina of the eye 10.

The scanner 80 and imaging lens 90 scan focused light in a raster manner across at least a portion of the retina. The scanner 80 is a two-axis scanner including a horizontal scanner for scanning the focused light horizontally across at least a horizontally extending portion of the retina and a vertical scanner for scanning the focused light vertically across at least a vertically extending portion of the retina. The horizontal scanner may include one of a rotatable polygonal mirror and a vibratable plane mirror and the vertical scanner may include a galvanometer scanner.

The scanner 80 is synchronised to the first light source 21 of light and to the second light source 22 by a controller (not shown).

The scanner 80 is synchronised by the controller (not shown) to the image sensor 130, the frame grabber 140 and the image processor 150.

A fixation target light emitting diode (not shown) may be positioned between the scanner 80 and the eye 10 to enable a subject to fix a direction of the eye for analysis.

A second incident light beam 221, subsequently emitted from the second light source 22 in a direction substantially perpendicular to the first light beam 211, is incident on a second face of the first optical beam combiner 30, opposed to the first face, at a second angle of incidence of substantially 45 degrees such that the second light beam has access to the first optical axis of the retinal function camera 200.

That is, a same portion of the retina is sequentially scanned with light from the first light source 21 and then from the second light source 22.

Light reflected from the retina at a back of the eye 10 re-passes through the imaging lens 90, is de-scanned by the scanner 80 and re-passes through the first focusing lens 70 to the optical beam splitter 60.

The optical beam splitter 60 directs light reflected from the retina to the orthogonal polarising filter 100. The polarising filter blocks light reflected from eye surfaces with substantially the same polarisation as the first light source 21 and the second light source 22.

A second focusing lens 110 focuses light reflected from the retina towards an optical filter 120.

The optical filter 120 is substantially confocal to the imaged retina. The optical filter may be a confocal aperture or an anti-confocal stop. Alternatively, the optical filter may be a combined confocal aperture and an anti-confocal stop forming an annular aperture. The filter blocks a portion of the reflected light from the retina reaching and being detected by the imaging sensor 130. For example, an anti-confocal filter will allow laterally scattered light signals to be detected while blocking on-axis light signals.

The imaging sensor 130 is sensitive to light emitted by the first light source 21 and the second light source 22. The imaging sensor converts the reflected light signals to electrical signals. The electrical signals are amplified, synchronised with the scanning means 80 and frame grabber 140 to form a time and space resolved image data frame.

The image processor 150 processes the image data frames. The image processor includes at least a computer and image processing and analysis software. Suitable software includes LabVIEW® image processing and analysis software available from National Instruments Corporation, Austin, Tex., United States of America.

Adaptive optics (not shown) may be used to correct for optical aberrations of the eye. A wave-front sensor such as a Shack-Hartmann wave-front sensor may be used to measure wave aberration of the light that is used to form the image. Wave-front compensation with a deformable mirror, before the raster scanner, corrects optical aberrations on the illuminating and return imaging light paths. The deformable mirror shape may be controlled by LabVIEW® software with data derived from the wave-front sensor.

A retinal metabolic image data based on haemoglobin oxygenation is obtained by using the first and second light sources with such wavelengths that the absorptivity of light of the first wavelength by oxygenated blood is greater than the absorptivity of light of the second wavelength and the absorptivity of light of the first wavelength by deoxygenated blood is less than the absorptivity of light of the second wavelength. The respective images of the portion of the retina illuminated with the respective wavelength bands are processed to determine isoreflective points of the respective images at which absorption of light of the first wavelength is substantially equal to absorption of light of the second wavelength and areas of the respective images having differential absorptivity for the first and second wavelengths. The haemoglobin oxygenation image data is isolated from the respective first and second wavelength images by subtracting the reflectivity at the isoreflective point from respective first and second wavelength images. The contrast of each portion of the processed images is then proportional to a difference in oxygenation of that respective point from the oxygenation of the isoreflective point, thereby providing retinal metabolic image data based on haemoglobin oxygenation.

The retinal metabolic haemoglobin oxygenation image data may be time synchronised to a heartbeat of the subject. Conventional synchronisation to an external signal, which may be used, includes synchronisation to an R-wave of an electrocardiogram or to pulse blood volume waveform detection with an infrared photoplethysmograph. However, in an embodiment of the invention, the haemoglobin oxygenation image data from a same portion of successive data frames is analysed to detect the haemoglobin oxygenation image data retinal arterial waveform to provide synchronisation with a cardiac cycle of the subject. For example, line 1 of a data frame may be compared with line 1 of successive data frames, line 2 may be compared with line 2 of successive data frames, line x may be compared with line x of successive data frames. The amplitude of successive line haemoglobin oxygenation image data is determined to generate a pattern or shape of successive line haemoglobin oxygenation image data. A steep rise waveform related to an arterial pulse is determined from the falling haemoglobin oxygenation image data slope. An amplitude foot at a junction between falling slope and steep arterial pulse on the haemoglobin oxygenation image data waveform may be identified and used as a retinal arterial waveform reference point. Optionally, an amplitude peak at a peak arterial pulse on the haemoglobin oxygenation image data waveform may be identified and used as the retinal arterial waveform reference point. Optionally again, an inflection point between an amplitude foot and an amplitude peak, i.e. when a second derivative of the waveform changes sign, on the haemoglobin oxygenation image data waveform may be identified and used as the retinal arterial waveform reference point. A period between a retinal arterial waveform reference point and a next retinal arterial waveform reference point defines a functional time period of a cardiac cycle, or heartbeat. The functional time period of a heartbeat may be defined from at least a portion of the image data.

A portion of the retinal metabolic image may be selected for analysis. The portion may be, for example, at least a pixel, a line scan, a data frame or an ophthalmologist-defined portion of the macula or optic disc. The portion may be each pixel of a data frame. The portion may be a subset of the haemoglobin oxygenation image data and may correspond to more haemoglobin oxygenation than the isoreflective point. Alternatively, the portion may be haemoglobin oxygenation image data corresponding to less haemoglobin oxygenation than the isoreflective point. The portion may be haemoglobin oxygenation image data that changes from more haemoglobin oxygenation than the isoreflective point to less haemoglobin oxygenation than the isoreflective point during the functional time period of a heartbeat. The haemoglobin oxygenation image data may be analysed to determine waveform characteristics of amplitude, pattern, shape, duration and response to optical signal stimuli. At least a portion of the image data may be analysed. A portion of the image data may be analysed over time. A portion of the image data may be analysed by Fourier analysis. A portion of the image data may be analysed over a functional time period of at least a heartbeat. A portion of the image data may be analysed over a functional time period of at least two heartbeats to determine average data waveform characteristics. Image alignment processing, optionally including pattern recognition, may be used.

The imaged eye may be position-stabilised by contra-lateral eye fixing on an external optical fixation target. That is, an optical fixation point may be used to help to maintain retinal image positional stability. The fixation point may be internal or external of the imaging optics. A typical fixation point is a light emitting diode. An optical fixation and optical signal stimulus laser 40 may be used instead of a light emitting diode source fixation point. The wavelength of the optical fixation point source may be selected between 488 nm and 760 nm. The optical fixation point wavelength may be centred substantially on 532 nm. The optical signal stimulus laser may be synchronised to the scanner 80. The optical signal stimulus laser may be synchronised to a retinal arterial waveform reference point.

A band-pass filter (not shown) may be used to block the green 532 nm optical signal stimulus light reflected from the eye from reaching the imaging sensor 130.

The optical signal stimulus laser may be modulated to generate an optical signal stimulus pattern on the retina of the eye 10.

That is, the optical fixation and optical signal stimulus laser 40 emits an optical stimulus light beam 401, centred substantially on a wavelength of 532 nm. The optical stimulus light beam 401 is incident at an angle of substantially 45 degrees on a first face of the second optical beam combiner 50 located on the first optical axis, downstream of the first optical beam combiner 30, on which the first incident beam 211 is incident on a second face, opposed to the first face, to combine the first incident beam 211 with the optical stimulus light beam 401 to form a combined beam 501 with access to the first optical axis. The combined beam passes sequentially through the optical beam splitter 60 and the first focusing lens 70 for correcting for refractive errors of the eye 10 to permit eventual focusing of the corrected combined beam 701 on a retina of the eye 10. The corrected combined beam 701 is incident on a vertical and horizontal scanner 80 to form a scanning beam 801 substantially on the first optical axis. The imaging lens 90 focuses the scanning beam 801 as a focused scanning beam 901 onto the retina of the eye 10.

Alternatively, light from the second light source may be combined with the optical stimulus light beam to form a combined beam.

The optical signal stimulus laser 40 may be synchronised to the scanner 80 by a controller (not shown). The optical signal stimulus laser 40 is modulated to generate an optical signal stimulus pattern on the retina of the eye 10.

Illuminating the internal fixation target light emitting diode or optical fixation and optical signal stimulus laser 40, allows retinal metabolic image changes in response to the optical signal stimulus to be imaged. The retinal metabolic image changes in response to the optical signal stimulus may be imaged and isolated by image subtraction from the background functional retinal metabolic image data obtained over a heartbeat, preferably after image alignment. Beat-to-beat variation of the background functional retinal metabolic image data obtained over a heartbeat may be averaged. The retinal metabolic image changes in response to the optical signal stimulus may be imaged and isolated by image subtraction from the averaged background functional retinal metabolic image data obtained over a heartbeat and fitted for amplitude and duration. The isolated retinal metabolic image changes in response to the optical signal stimulus may be analysed to determine waveform characteristics of latency, amplitude, pattern, shape, and duration. The isolated retinal metabolic image changes in response to the optical signal stimulus may be displayed in image, numerical or graphic format. The background functional retinal metabolic image data obtained over a heartbeat is dynamically varying and a function of the arterial haemoglobin oxygen supply and retinal metabolic oxygen consumption. The isolation of a subtle alteration in retinal tissue oxygenation due to an optical signal stimulus from a dynamically varying background is enhanced by the functional time synchronised reference background functional retinal metabolic image data.

An array of light emitting diodes arranged in a grid may be used to allow multiple points on the retina of the eye 10 to be stimulated simultaneously. The optical signal stimulus laser 40 may be modulated to generate an optical signal stimulus pattern on the retina of the eye 10. The optical signal stimulus laser 40 may be modulated to generate an optical signal stimulus pattern on the retina of the eye 10 with a single optical fixation point. The optical signal stimulus laser 40 may be modulated to generate an optical signal stimulus pattern on the retina of the eye 10 with a single optical fixation point and then switch on and off a pattern while retaining a single optical fixation point. The duration of illumination may be controlled. The light intensity may be controlled.

An array of external light emitting diodes may be arranged in a circular grid as an external optical fixation target. Sequentially fixing the eye on sequentially illuminated light emitting diodes allows the retinal periphery to be imaged.

The retinal metabolic image changes over the duration of a heartbeat. With the arrival of a retinal arterial pulse there is an increase of retinal haemoglobin oxygenation. This is followed by a fall in retinal haemoglobin oxygenation, due to oxygen consumption within the metabolically active retinal tissue, before the next retinal arterial pulse. Retinal metabolic image data may be analysed over a functional time period of a heartbeat to provide an objective assessment of retinal metabolism. The retinal metabolic image data is derived from the dynamic function of arterial oxygenated haemoglobin supply and the retinal metabolic oxygen consumption. Changes in the arterial oxygenated haemoglobin supply may be detected. If the cardiac output is impaired then tissue perfusion with oxygenated blood will be impaired. Retinal metabolic image data may detect a reduced cardiac output. Retinal metabolic image data may detect a reduced cardiac output secondary to blood loss. Retinal metabolic image data may be analysed over a functional time period of a heartbeat to provide an objective assessment of retinal metabolism with a reduced cardiac output.

Changes in the arterial oxygenated haemoglobin supply between the heart and the retina may be detected. A cerebral artery haemorrhage may increase the intracranial pressure. Increased intracranial pressure may impair both retinal arterial supply and retinal vein drainage. A cerebral artery occlusion does not necessarily increase intracranial pressure. Retinal metabolic image data may be analysed over a functional time period of a heartbeat to provide an objective assessment of retinal metabolism with raised intracranial pressure. Characteristics of retinal metabolic image data analysed over a functional time period of a heartbeat may help to differentiate between a cerebral artery occlusion and a cerebral artery haemorrhage.

Retinal metabolic image data may be analysed over time. The time period may be a functional time period, such as a heartbeat or a discrete time interval. This generates an objective assessment of retinal metabolism by generating numerical or graphical output of retinal metabolism compared with the images requiring subjective assessment in the prior art.

The retinal metabolic image changes in response to stimulus optical signals may be isolated by image subtraction from the background functional retinal metabolic image data obtained over a heartbeat.

A resulting isolated retinal metabolism response to the optical stimulation may be analysed for one or more of latency between the optical stimulation and the metabolism response and the amplitude, pattern, shape and duration of a waveform of the response.

This invention overcomes the lack of an objective assessment of retinal metabolism by analysing the retinal haemoglobin oxygenation image data over a functional time period of at least a portion of a heartbeat to produce an objective assessment of retinal metabolism.

This invention provides the advantage of isolating retinal haemoglobin oxygenation image data from multi-spectral retinal images, analysing the data over time, determining retinal metabolic response to optical stimuli and providing an objective assessment of retinal metabolism. The invention enables earlier diagnosis of eye disease than in the prior art. The invention enables objective monitoring of eye disease and enables objective monitoring of eye disease response to therapy. Clinical trials may objectively evaluate the effects of therapeutic agents on retinal metabolism. Clinical trials may objectively evaluate the effects of therapeutic agents on retinal metabolic response to optical stimulation.

Alternative embodiments of the invention can be implemented as a computer program product for use with a computer system, the computer program product being, for example, a series of computer instructions stored on a tangible data recording medium, such as a diskette, CD-ROM, ROM, or fixed disk, or embodied in a computer data signal, the signal being transmitted over a tangible medium or a wireless medium, for example microwave or infrared. The series of computer instructions can constitute all or part of the functionality described above, and can also be stored in any memory device, volatile or non-volatile, such as semiconductor, magnetic, optical or other memory device.

Although the present invention has been described with reference to preferred embodiments, workers skilled in the art will recognize that changes may be made in form and detail without departing from the spirit and scope of the invention.

I claim:

1. A method of analysing retinal metabolism over at least a portion of a cardiac cycle, the method comprising using a retinal function camera to perform the steps of:
   a. illuminating a portion of a retina of an eye with light of a first wavelength;
   b. producing a first image of the portion of the retina illuminated with the light of the first wavelength;
   c. illuminating the portion of the retina with light of a second wavelength, the first and second wavelengths being selected such that absorptivity of light of the first wavelength by oxygenated blood is greater than absorptivity of light of the second wavelength and the absorptivity of light of the first wavelength by deoxygenated blood is less than absorptivity of light of the second wavelength;
   d. producing a second image of the portion of the retina illuminated with the light of the second wavelength;
   e. processing the first and second images with image processing means to map relative oxygenation of the portion of the retina as an indication of retinal metabolic function of the portion of the retina; and
   f. repeating steps a) to e) within the at least a portion of a cardiac cycle to analyse metabolic function changes of the portion of the retina to detect a haemoglobin oxygenation image data retinal arterial waveform within the at least a portion of a cardiac cycle to provide synchronisation with a cardiac cycle of a subject for analysing retinal metabolic image data over the at least a portion of the cardiac cycle.

2. A method as claimed in claim 1, wherein the step of illuminating the portion of the retina with light of a first wavelength comprises providing a first light source and emitting light of the first wavelength and providing scanning means to produce a scanning beam and scanning the portion of the retina with light from the first light source.

3. A method as claimed in claim 2, wherein the step of illuminating the portion of the retina with light of a second wavelength comprises providing: a second light source and emitting light of the second wavelength and first optical beam combiner means and selectively directing light from the first light source and from the second light source to the scanning means to produce a scanning beam and scanning the portion of the retina with light from the second light source subsequently to scanning the portion of the retina with light from the first light source.

4. A method as claimed in claim 2, wherein at least one of the first light source and the second light source is synchronised with the scanning means.

5. A method as claimed in claim 2, including a step of providing first focusing means and focusing the scanning beam from the scanning means onto the at least a portion of the retina with the first focusing means.

6. A method as claimed in claim 5, including a step of providing refractive error correcting means and correcting for refractive errors of the eye with the refractive error correcting means, to permit focusing of the scanning beam on the at least a portion of the retina.

7. A method as claimed in claim 6, wherein the step of providing refractive error correcting means comprises providing adaptive optics and correcting for optical aberrations of the eye.

8. A method as claimed in claim 6, wherein the step of providing refractive error correcting means comprises providing wave-front sensor means and wave-front compensation means.

9. A method as claimed in claim 8, wherein the step of providing wave-front compensation means comprises providing deformable mirror means.

10. A method as claimed in claim 5, wherein the step of producing first and second images comprises the steps of:
    providing beam splitter means for splitting a beam reflected from the at least a portion of the retina when illuminated by light of the first wavelength and light of the second wavelength to form a split beam; and
    providing image sensor means and second focusing means and focusing the split beam on the image sensor means for sensing an image of the at least a portion of the retina and image capture means for capturing the sensed image.

11. A method as claimed in claim 10, wherein the step of providing image capture means comprises providing frame grabber means.

12. A method as claimed in claims 10, wherein the scanning means is synchronised with at least one of the image sensor means, the image capture means and the image processing means.

13. A method as claimed in claim 1, wherein the step of illuminating the portion of the retina with light of the first wavelength comprises illuminating the portion of the retina with light of wavelengths centred on one of 830 nm, 850 nm and 910 nm.

14. A method as claimed in claim 1, wherein the step of illuminating the portion of the retina with light of the second wavelength comprises illuminating the portion of the retina with light of wavelengths centred on one of 635 nm, 670 nm and 760 nm.

15. A method as claimed in claim 1, wherein the step of processing the first and second images comprises determining isoreflective points of the respective images at which absorption of light of the first wavelength is substantially equal to absorption of light of the second wavelength and determining areas of the respective images having differential absorptivity for the first and second wavelengths; isolating haemoglobin oxygenation image data from the first and second wavelength images by subtracting the isoreflective point from respective first and second wavelength images, the contrast of each portion of the processed images thereby being proportional to a difference in oxygenation of that portion of the processed images from the oxygenation of the isoreflective point, to obtain retinal metabolic image data based on haemoglobin oxygenation.

16. A method as claimed in claim 1, wherein step f) further comprises determining from the metabolic function changes a waveform reference point in a haemoglobin oxygenation image data waveform corresponding to a cardiac cycle.

17. A method as claimed in claim 16, wherein the step of determining a waveform reference point comprises determining an amplitude trough between a trailing edge and a leading edge of an arterial pulse of the haemoglobin oxygenation image data waveform.

18. A method as claimed in claim 16, wherein the step of determining a waveform reference point comprises determining an amplitude peak of an arterial pulse of the haemoglobin oxygenation image data waveform.

19. A method as claimed in claim 16, wherein the step of determining a waveform reference point comprises determining an inflection point between an amplitude trough and an amplitude peak of an arterial pulse of the haemoglobin oxygenation image data waveform.

20. A method as claimed in claim 16, comprising determining oxygenation changes associated with the cardiac cycle.

21. A method as claimed in claim 20, comprising determining characteristics of at least one of amplitude, pattern, shape and duration of the cardiac cycle.

22. A method as claimed in claim 20, wherein the step of determining oxygenic changes comprises using Fourier analysis for determining a cardiac cycle waveform.

23. A method as claimed in claims 20, wherein step f) further comprises subtracting effects of changes in oxygenation caused by the cardiac cycle to determine metabolic function of the at least a portion of the retina independently of oxygenation changes caused by the cardiac cycle.

24. A method as claimed in claim 16, including a further step of subjecting the at least a portion of the retina to optical stimulation and analysing effects of the optical stimulation on retinal metabolic function.

25. A method as claimed in claim 24, wherein the optical stimulation of the at least a portion of the retina is synchronised with reference to a waveform reference point.

26. A method as claimed in claim 24, wherein step f) further comprises subtracting effects of changes in oxygenation caused by the cardiac cycle from the effects of changes in oxygenation caused by the optical stimulation to isolate changes in retinal metabolism caused by the optical stimulation.

27. A method as claimed in claim 26, comprising analysing isolated responses of retinal metabolism caused by the optical stimulation to determine waveform characteristics of at least one of latency between the optical stimulation and the retinal metabolism response, amplitude, pattern, shape and duration of the response.

28. A method as claimed in claim 24, wherein the step of subjecting the at least a portion of the retina to optical stimulation comprises providing an optical signal stimulus light source; and second beam combining means and combining a light beam from the optical signal stimulus light source selectively with one of light of the first wavelength and light of the second wavelength.

29. A method as claimed in claim 28, wherein the step of providing an optical signal stimulus light source comprises providing an array of light-emitting diodes and one of simultaneously or sequentially stimulating a plurality of points on the at least a portion of the retina.

30. A method as claimed in claim 28, wherein the optical signal stimulus light source is modulated to generate an optical signal stimulus pattern on the at least a portion of a retina.

31. A method as claimed in claim 28, wherein the step of providing an optical signal stimulus light source comprises providing an optical signal stimulus laser.

32. A method as claimed in claim 24, comprising evaluating effects of therapeutic agents on retinal metabolic response to optical stimulation.

33. A method as claimed in claim 1, comprising determining cardiac function.

34. A method as claimed in claim 1, comprising determining cerebral arterial circulatory function.

35. A method as claimed in claim 1 comprising evaluating effects of therapeutic agents on retinal metabolism.

36. A retinal function camera comprising: a first source of light of a first wavelength band; a second source of light of a second wavelength band, the absorptivity of light of the first wavelength band by oxygenated blood being greater than the absorptivity of light of the second wavelength band and the absorptivity of light of the first wavelength band by deoxygenated blood being less than the absorptivity of light of the second wavelength band; an optical signal stimulus light source; means for focusing light from the optical signal stimulus light source and selectively from the first and second sources onto a portion of a retina of an eye; imaging means for producing respective images of the portion of the retina illuminated with the respective wavelength bands and stimulated by the optical signal stimulus light source; and processing means adapted to process the respective images obtained by the imaging means to determine isoreflective points of the respective images at which absorption of light of the first wavelength is substantially equal to absorption of light of the second wavelength and areas of the respective images having differential absorptivity for the first and second wavelengths, repeatedly to obtain a retinal function image based on haemoglobin oxygenation within at least a portion of a cardiac cycle to analyse metabolic functional changes of the portion of the retina to detect a haemoglobin oxygenation image data retinal arterial waveform within the at least a portion of a cardiac cycle to provide synchronisation with a cardiac cycle of a subject for analysing retinal metabolic image data over the at least a portion of the cardiac cycle when the retina is subjected to optical stimulation.

37. A retinal function camera as claimed in claim 36, wherein the optical signal stimulus light source is an optical signal stimulus laser.

38. A retinal function camera as claimed in claim 36, further comprising scanning means arranged for producing a scanning beam for scanning the portion of the retina with light from the optical signal stimulus light source and selectively from the first and second sources.

39. A retinal function camera as claimed in claim 38, further comprising first optical beam combiner means arranged for selectively directing light from the first light source and from the second light source to the scanning means.

40. A retinal function camera as claimed in claim 38, further comprising first synchronisation means arranged for synchronising at least one of the first light source and the second light source with the scanning means.

41. A retinal function camera as claimed in claim 38, further comprising refractive error correcting means arranged for correcting for refractive errors of the eye to permit focusing of the scanning beam on the at least a portion of the retina.

42. A retinal function camera as claimed in claim 41, wherein the refractive error correcting means comprises adaptive optics arranged for correcting for optical aberrations of the eye.

43. A retinal function camera as claimed in claim 41, wherein the refractive error correcting means comprises wave-front sensor means and wave-front compensation means.

44. A retinal function camera as claimed in claim 43, wherein the wave-front compensation means comprises deformable mirror means.

45. A retinal function camera as claimed in claim 38, further comprising beam splitter means arranged for splitting a beam reflected from the at least a portion of the retina when illuminated by light of the first wavelength band and light of the second wavelength band to form a split beam; image sensor means and second focusing means arranged for focusing the split beam on the image sensor means for sensing an image of the at least a portion of the retina and image capture means for capturing the sensed image.

46. A retinal function camera as claimed in claim 45, further comprising second synchronisation means arranged for synchronising at least one of the image sensor means, the image capture means and image processing means with the scanning means.

47. A retinal function camera as claimed in claim 46, wherein the image capture means comprises frame grabber means.

48. A retinal function camera as claimed in claim 36, wherein the first wavelength band comprises wavelengths centred on one of 830 nm, 850 nm and 910 nm.

49. A retinal function camera as claimed in claim 36, wherein the second wavelength band comprises wavelengths centred on one of 635 nm, 670 nm and 760 nm.

50. A tangible computer readable medium comprising computer executable software code for analysing retinal metabolism over at least a portion of a cardiac cycle, wherein the code is configured to perform the steps of:
   a. illuminating a portion of a retina of an eye with light of a first wavelength;
   b. producing a first image of the portion of the retina illuminated with the light of the first wavelength;
   c. illuminating the portion of the retina with light of a second wavelength, the first and second wavelengths being selected such that absorptivity of light of the first wavelength by oxygenated blood is greater than absorptivity of light of the second wavelength and the absorptivity of light of the first wavelength by deoxygenated blood is less than absorptivity of light of the second wavelength;
   d. producing a second image of the portion of the retina illuminated with the light of the second wavelength;
   e. processing the first and second images with image processing means to map relative oxygenation of the portion of the retina as an indication of retinal metabolic function of the portion of the retina; and
   f. repeating steps a) to e) within the at least a portion of a cardiac cycle to analyse metabolic function changes of the portion of the retina to detect a haemoglobin oxygenation image data retinal arterial waveform within the at least a portion of a cardiac cycle to provide synchronisation with a cardiac cycle of a subject for analysing retinal metabolic image data over the at least a portion of the cardiac cycle.

* * * * *